United States Patent

Blendinger

[11] Patent Number: 6,133,574
[45] Date of Patent: Oct. 17, 2000

[54] RADIATION-ELECTRICAL TRANSDUCER

[75] Inventor: Heinz-Jürgen Blendinger, Erlangen, Germany

[73] Assignee: Siemens Aktiengesellschaft, Munich, Germany

[21] Appl. No.: 09/242,180

[22] PCT Filed: Jul. 1, 1998

[86] PCT No.: PCT/DE98/01807

§ 371 Date: Mar. 1, 1999

§ 102(e) Date: Mar. 1, 1999

[87] PCT Pub. No.: WO99/01783

PCT Pub. Date: Jan. 14, 1999

[30] Foreign Application Priority Data

Jul. 2, 1997 [DE] Germany .......................... 197 28 237

[51] Int. Cl.⁷ .................. G01T 1/24; H01L 31/00
[52] U.S. Cl. ..................... 250/370.11; 257/428
[58] Field of Search .................. 250/370.01, 370.11, 250/370.14; 257/428

[56] References Cited

U.S. PATENT DOCUMENTS

| | | | |
|---|---|---|---|
| 4,734,588 | 3/1988 | Akai | 250/370.11 |
| 5,041,729 | 8/1991 | Takahashi et al. | 250/370.11 |
| 5,629,524 | 5/1997 | Stettner et al. | 250/370.11 |

FOREIGN PATENT DOCUMENTS

OS 30 09 723   9/1981   Germany .

OTHER PUBLICATIONS

"Design of Integrated Radiation Detectors with a–Si Photodiodes on Ceramic Scintillators for use in X–ray Computed Tomography," Takahashi et al., IEEE Trans. on Nucl. Sci., vol. 37, No. 3 Jun.—1990, pp.1478–1482.

*Primary Examiner*—F. L. Evans
*Attorney, Agent, or Firm*—Hill & Simpson

[57] ABSTRACT

A transducer is composed of a scintillator and a c-Si photodiode chip with the scintillator or luminophore serving directly as a carrier for the photodiode chip, whose active side is electrically contacted via contact runs on the scintillator.

3 Claims, 1 Drawing Sheet

RADIATION-ELECTRICAL TRANSDUCER

BACKGROUND OF THE INVENTION

1. Field of the Invention

The present invention is directed to a radiation-electrical transducer of the type having a luminophore that serves as carrier for at least one light-electrical transducer that is mechanically connected to the luminophore.

2. Description of the Prior Art

In X-ray technology, radiation-electrical transducers are employed that have a luminophore that converts the absorbed X-radiation into light, this light being converted into an electrical signal in a photosensitive transducer, for example, a photodiode. The overall transducer thus represents a detector for the received radiation intensity.

A scintillator can be provided as luminophore and a c-Si photodiode can be provided as photodiode.

German OS 30 09 723 discloses a transducer of the type initially cited. Nothing is stated about the type of light-electrical transducer and about the electrical contacting of the light-electrical transducer.

U.S. Pat. No. 4,734,588 also discloses a transducer that has a carrier on which a photodiode array together with the electrodes required for its electrical contacting is attached. Scintillators allocated to the individual photodiodes are glued to the photodiode array. The active sides of the photodiodes thereby face toward the scintillator or away from it dependent on the exemplary embodiment.

It is known from Tetsuhiko Takahashi et al., "Design of Integrated Radiation Detectors with a-Si Photodiodes on Ceramic Scintillators for Use in X-Ray Computed Tomography", IEEE Transactions on Nuclear Science, Vol. 37, No. 3, June 1990, pages 1478–1482, that both c-Si photodiodes as well as a-Si photodiodes can be utilized in radiation-electrical transducers.

SUMMARY OF THE INVENTION

An object of the present invention is to provide a radiation-electrical transducer composed of a luminophore and a photodiode as simply as possible.

This object is inventively achieved in a transducer wherein the luminophore serves as carrier for at least one photodiode and for the contacts required for its electrical contacting. A separate carrier material, for example a substrate or a printed circuit board, can be omitted.

DESCRIPTION OF THE PREFERRED EMBODIMENTS

Figure 1:
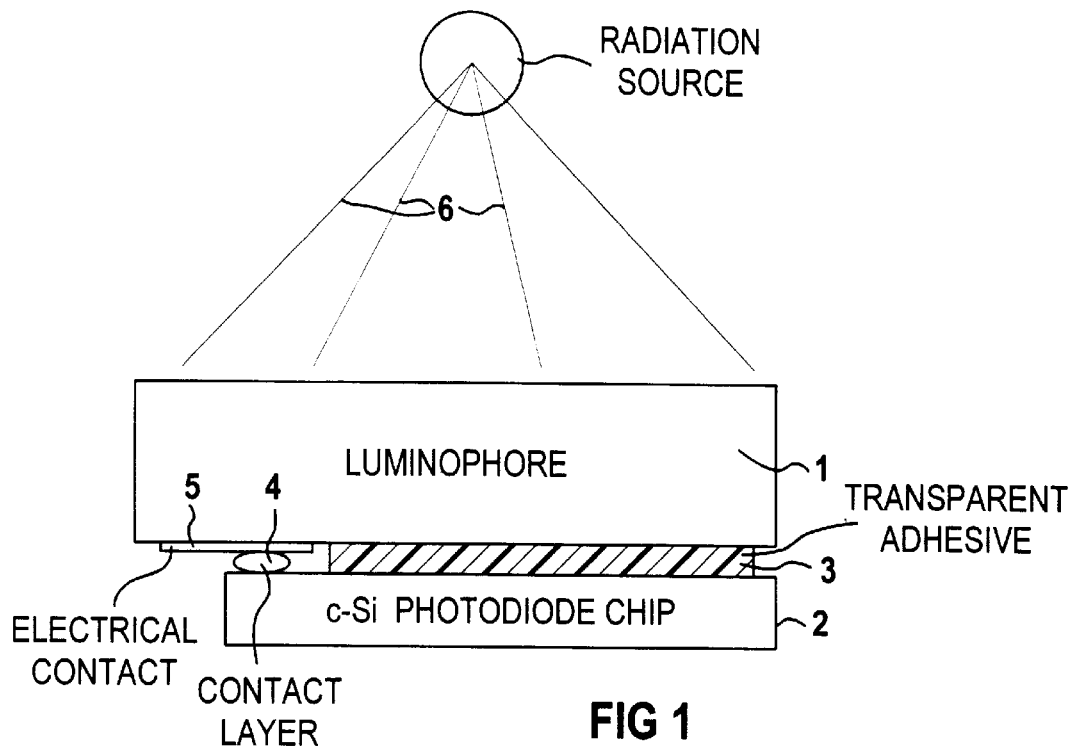
FIG. 1 is a side sectional view of a radiation-electrical transducer constructed in accordance with the principles of the present invention.
Figure 2:
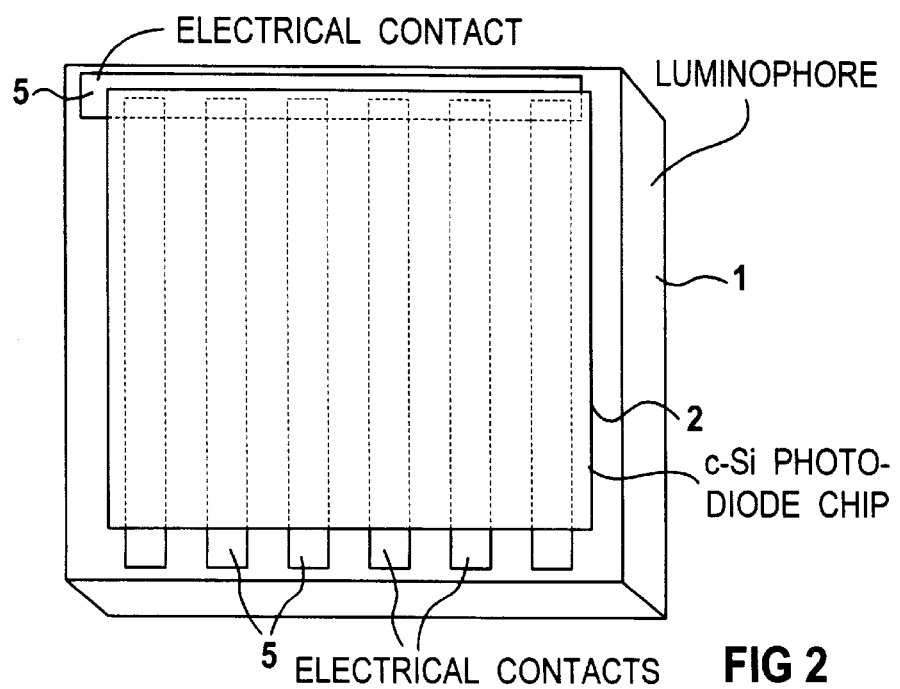
FIG. 2 is a view from below of a further version of the radiation-electrical transducer of FIG. 1.

FIGS. 1 and 2 show a luminophore 1, particularly a ceramic scintillator, that carries a c-Si photodiode chip 2 on its underside. The photodiode chip 2 is joined to the luminophore 1 with the assistance of a transparent adhesive 3. The electrical contacting of the photodiode chip 2 ensues with the assistance of a contact layer 4 that produces a conductive connection from the photodiode chip 2 to contacts 5 of, for example, gold that are vapor-deposited on the luminophore 1. Proceeding from these contacts 5, which, for example, can be a matter of contact tracks, further electrical connection ensues with the assistance of, for example, gold wires in a way that is not shown.

The active side of the c-Si photodiode chip 2, i.e. that side that is light-sensitive as a result of corresponding method steps in the manufacture, for example diffusion processes, faces toward the luminophore 1. The contact layer 4 is fashioned as what is referred to as a contact bump that is electrically contacted to the contacts 5.

A module according to FIGS. 1 and 2 can be installed, for example, in computer tomography or in baggage scanners in a collimator. Such a module, however, is generally suited for all types of devices in which radiation is converted into electrical signals. In FIG. 1, the lines 6 indicate radiation, for example X-rays.

The photodiode chip 2 is formed by a matrix of photodiodes, whereby the contacts 5 are present in a corresponding number. It is also possible within the scope of the invention to connect only one photodiode to a luminophore in the disclosed way.

Although modifications and changes may be suggested by those of ordinary skill in the art, it is the intention of the inventor to embody within the patent warranted hereon all changes and modifications as reasonably and properly come within the scope of his contribution to the art.

I claim as my invention:

1. A radiation-electrical transducer comprising:

a c-Si photodiode having an active side;

a luminophore serving as a carrier for said c-Si photodiode, said luminophore having a plurality of electrical contacts thereon and said luminophore being mechanically connected to said active side of said c-Si photodiode and in electrical contact with said c-Si photodiode via said plurality of contacts.

2. A radiation-electrical transducer as claimed in claim 1 further comprising a transparent adhesive disposed between said c-Si photodiode and said luminophore and mechanically connecting said c-Si photodiode to said luminophore.

3. A radiation-electrical transducer as claimed in claim 1 comprising a photodiode chip comprising a plurality of c-Si photodiodes substantially identical to said c-Si photodiode, and wherein said plurality of contacts on said luminophore comprises a plurality of contacts for respectively electrically contacting said c-Si photodiodes in said c-Si photodiode chip.

* * * * *